United States Patent [19]
Burn et al.

[11] Patent Number: 5,556,954
[45] Date of Patent: Sep. 17, 1996

[54] HEMATOPOIETIC STEM CELL SPECIFIC GENE EXPRESSION

[75] Inventors: Timothy C. Burn, Bedford; Anne B. Satterthwaite, Brighton; Daniel G. Tenen, Boston, all of Mass.

[73] Assignee: Beth Israel Hospital Boston Association, Boston, Mass.

[21] Appl. No.: 990,965

[22] Filed: Dec. 15, 1992

Related U.S. Application Data

[63] Continuation-in-part of Ser. No. 837,776, Feb. 13, 1992, abandoned.
[51] Int. Cl.$^6$ .............................. C07H 21/04; C12N 5/10; C12N 15/85
[52] U.S. Cl. .................. 536/24.1; 435/240.2; 435/320.1
[58] Field of Search ................................. 536/23.1, 24.1; 435/240.2, 320.1

[56] References Cited

U.S. PATENT DOCUMENTS 4,959,313 10/1990 Taketo ..................................... 435/69.1

OTHER PUBLICATIONS

Shelley et al., PNAS (USA) 88:10525–10529 (Dec. 1991).
Nolta et al., Exp. Hematol. 20(9): 1065–1071 (1992).
Day, *The Washington Post*, "Washington Business" Section, Nov. 7, 1994.
Pahl, Heike L. et al., "Optimization of Transient Transfection into Human Myeloid Cell Lines Using a Luciferase Reporter Gene," *Exp. Hematol.* 19:1038–1041 (1991).
Arnaout, M. Amin et al., "Amino Acid Sequence of the Alpha Subunit of Human Leukocyte Adhesion Receptor Mol (Complement Receptor Type 3)," *J. of Cell Biology* 106:2153–2158 (1988).
Shelley, C. Simon et al., "The promoter of the CD11b gene directs myeloid–specific and developmentally regulated expression," *Proc. Natl. Acad. Sci. USA* 88:10525–10529 (1991).
Pahl, H. L. et al., "Characterization of the Myeloid–Specific CD11b Promoter," *Blood* 79(4):865–870 (1992).
Pahl, H. L. et al., "The CD11B Promoter Directs Monocytic expression of a Reporter Gene in Transgenic Mice," *The American Society of Hematology*, 33rd Annual Meeting, ASH Abstract (1991).
Satyabhama, S. et al., "Short–Term Efficient Expression of Transfected DNA in Human Hematopoietic Cells by Electroporation: Definition of Parameters and Use of Chemical Stimulators," *DNA*, 7(3):203–209 (1988).
Brown, J. et al., "The gene encoding the stem cell antigen, CD34, is conserved in mouse and expressed in haemopoietic progenitor cell lines, brain, and embryonic fibroblasts," *Int. Immunol.*, 3:175–184 (1991).

*Primary Examiner*—Stephanie W. Zitomer
*Attorney, Agent, or Firm*—Hamilton, Brook, Smith & Reynolds, P.C.

[57] ABSTRACT

The subject application relates to a hematopoietic stem cell specific promoter and to a hematopoietic stem cell specific enhancer and to uses therefor. The invention also includes a hematopoietic stem cell specific promoter-heterologous gene construct, where the expression of the heterologous gene is under the control of the myeloid cell type specific promoter. Additionally, the application is drawn to a method of expressing a heterologous gene in a hematopoietic stem cell. The invention further includes a method of expressing a selected heterologous gene product in hematopoietic stem cells in an individual. The invention also includes a transgenic non-human mammal in which the hematopoietic stem cells express a protein encoded by a heterologous gene. Finally the invention includes a method for identifying factors which can regulate hematopoietic stem cell specific transcription.

12 Claims, 5 Drawing Sheets

TAGGATGATGGTGATGGGAACTAAATGGGAAATATGGAAGGTCACAGGAAAAGTTAACACAAGTTAGCAAATTAACATAACACAA  -451
                                            ETS  MYB       MYB
                                                 -390 bp

AAAGGTCTTGCAGGAAAAAAGAAGAAAGAAAAAGTCTCCAAGAATGGTTTGGACAGCCAAATGAATACTTATAGTCAC  -361
              ETS

GTATACCTGCTCACTCCTGACGCTTCACTCACACAGAGATCTGGTGAGCTATGACTAAATGTGCCACATTGTGGTTAAGTTTT  -271
      ETS                                    GATA

ACCTGATTAACGAAATGCTCACACTTCTAAACTGAGGTCCTTACAGTAGATTCCTTTGCAAGATTGTTACTGGCTTACAACTTAAAAAT  -181
                                              ETS
                                           -131 bp

AAAGGAAAATCACAAGGAAAGAAAAGTGGGGAAAAAATGGAAGCTTGAAGAAGTGGAAGTGGATGGGAAGAAGTGGAAGCTTGAACGAGGCATCTGAACGAGGCATCTGAGACCCGAACAAACCTCCA  -91
 ETS        ETS
           -68bp

TAAAAGTTAAGTGGAAGTGGAGCTTGAAGAAGTGGATGGGAAGAAGTGGGATGCTTGAAGAAGTGGATGGGAAGCTGCAGGGAGCTCAAGTTAGTAGCAGC  -1
     MYB
         →
CCTTTTTTGGCCTCGACGGCGGCAACCCAGCCTCCCCTCCCAGCCTCCCTCCCAGGGGAGCTCAAGTTAGTAGCAGC  +90

CAAGGAGAGGCGCTTGCCTTGCCAAGACTAAAAGGGAGAAGAGAGGGAAAAAAGCAAGAATCCCCACCCTCTCCCGGCGGAGG  +180

GGGCGGGAAGAGCGCGGTCTTCCTGGCCAAGCCGAGTAGTGTCTTCCACTCGGTGCGTCTCTCTAGGAGCCGGGAAGGATGCTGGTCCGC  +270

AGGGGCGGCGCGGGCCCAGGATGCCTGGACCGGCGCTTGCTTGCTGAGTTTGCTGCgtgagtaccgcccgccgccccggc  +336

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 540 base pairs
        ( B ) TYPE: nucleic acid
        ( C ) STRANDEDNESS: double
        ( D ) TOPOLOGY: linear     ( i i ) MOLECULE TYPE: DNA (genomic)

( x i ) SEQUENCE DESCRIPTION: SEQ ID NO:1:

```
TAGGATGATG  GTGATGGGGA  ACTAAATGGG  GAAATATGGA  AGGTCACAGG  AAAAGTTAAC   60

ACAAGTTAGC  AAAAAGTTAA  CATAACACAA  AAAGGTCTTG  CAGGAAAAAA  AAAAGAAAAG  120

AAAAGAAAGA  AAAAGTCTCC  AAGAATGGTT  TGGACAGCCA  AAATGAATAC  TTATAGTCAC  180

GTATACCTGC  TCACTCCTGA  CGCTTCACTC  ACACACAGCA  CAGGATCTGG  TGAGGCTATC  240

ACTAAATGTG  CCACATTGTG  GTTAAGTTTT  ACCTGATTAA  CGAAATGCTC  ACACTTCTAA  300

ACTGAGGTCC  TTACAGTAGA  TTCCTTTTGC  AAGATTGTTA  CTGGCTTACA  ACTTAAAAAT  360

AAAGGAAAAT  CACAAGGAAA  GAAAAGTGGG  GAAAAAATCG  GAGGAAACTT  GCCCCTGCCC  420

TGGCCACCGG  CAAGGCTGCC  ACAAAGGGGT  TAAAAGTTAA  GTGGAAGTGG  AGCTTGAAGA  480

AGTGGGATGG  GGCCTCTCCA  GAAAGCTGAA  CGAGGCATCT  GGAGCCCGAA  CAAACCTCCA  540
```

( 2 ) INFORMATION FOR SEQ ID NO:2:

(i) SEQUENCE CHARACTERISTICS:
   (A) LENGTH: 32 base pairs
   (B) TYPE: nucleic acid
   (C) STRANDEDNESS: double
   (D) TOPOLOGY: linear (ii) MOLECULE TYPE: DNA (genomic)

(xi) SEQUENCE DESCRIPTION: SEQ ID NO:2:

GGGGATCCTT GAAGAAGTGG GATGGGGCCT CT                            32

(2) INFORMATION FOR SEQ ID NO:3:

(i) SEQUENCE CHARACTERISTICS:
      (A) LENGTH: 17 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:3:

GCTACTAACT TGAGCTC                                              17

(2) INFORMATION FOR SEQ ID NO:4:

(i) SEQUENCE CHARACTERISTICS:
      (A) LENGTH: 900 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:4:

```
TAGGATGATG GTGATGGGGA ACTAAATGGG GAAATATGGA AGGTCACAGG AAAAGTTAAC    60
ACAAGTTAGC AAAAAGTTAA CATAACACAA AAAGGTCTTG CAGGAAAAAA AAAAGAAAAG   120
AAAAGAAAGA AAAAGTCTCC AAGAATGGTT TGGACAGCCA AAATGAATAC TTATAGTCAC   180
GTATACCTGC TCACTCCTGA CGCTTCACTC ACACACAGCA CAGGATCTGG TGAGGCTATC   240
ACTAAATGTG CCACATTGTG GTTAAGTTTT ACCTGATTAA CGAAATGCTC ACACTTCTAA   300
ACTGAGGTCC TTACAGTAGA TTCCTTTTGC AAGATTGTTA CTGGCTTACA ACTTAAAAAT   360
AAAGGAAAAT CACAAGGAAA GAAAAGTGGG GAAAAAATCG GAGGAAACTT GCCCCTGCCC   420
TGGCCACCGG CAAGGCTGCC ACAAAGGGGT TAAAAGTTAA GTGGAAGTGG AGCTTGAAGA   480
AGTGGGATGG GGCCTCTCCA GAAAGCTGAA CGAGGCATCT GGAGCCCGAA CAAACCTCCA   540
CCTTTTTTGG CCTCGACGGC GGCAACCCAG CCTCCCTCCT AACGCCCTCC GCCTTTGGGA   600
CCAACCAGGG GAGCTCAAGT TAGTAGCAGC CAAGGAGAGG CGCTGCCTTG CCAAGACTAA   660
AAAGGGAGGG GAGAAGAGAG GAAAAAAGCA AGAATCCCCC ACCCCTCTCC CGGGCGGAGG   720
GGGCGGGAAG AGCGCGTCCT GGCCAAGCCG AGTAGTGTCT TCCACTCGGT GCGTCTCTCT   780
AGGAGCCGCG CGGGAAGGAT GCTGGTCCGC AGGGGCGCGC GCGCAGGGCC CAGGATGCCG   840
CGGGGCTGGA CCGCGCTTTG CTTGCTGAGT TTGCTGCGTG AGTACCGCCC GCGCGCCGGC   900
```

HEMATOPOIETIC STEM CELL SPECIFIC GENE EXPRESSION

GOVERNMENT SUPPORT

The work described herein was supported in part by the National Institutes of Health Grant No. CA34183. The United States Government has rights in the subject invention.

RELATED APPLICATION

This application is a Continuation-In-Part of U.S. patent application, Ser. No. 07/837,776 filed Feb. 13, 1992, now abandoned, in favor of a U.S. File Wrapper Continuing application, Ser. No. 08/020,465 filed Feb. 19, 1993, now abandoned the contents of which are incorporated herein by reference.

BACKGROUND OF THE INVENTION

Gene expression is accomplished by the transcription of genetic information from DNA to RNA and then the translation of RNA to protein molecules. In transcription, RNA molecules are synthesized by using the base sequence of one strand of DNA as a template in a polymerization reaction that is catalyzed by RNA polymerases. RNA polymerases bind to a DNA strand at particular sites called promoters.

Transcriptional regulation is one mechanism of controlling gene expression. Some promoters are competent to support initiation by RNA polymerase, although repressor proteins may act to prevent the initiation process. In other cases, the polymerase itself is not adequate and ancillary proteins (e.g. transcription factors) are necessary for initiation to occur.

Hematopoiesis (i.e., blood cell development) involves complex transcriptional and translational controls. Pluripotent stem cells in the bone marrow divide to form committed precursor cells, which mature along distinct pathways. The different types of blood cells are produced in different numbers, and the production of each must be regulated individually to meet changing needs. An understanding of these controls is still very incomplete.

A central objective in the study of hematopoiesis is the isolation of factors governing cell commitment to differentiation along a specific lineage. In several other systems, transcription factors have been shown to play a role in cellular differentiation. More recently, transcription factors have also been implicated in normal myeloid (monocytic, neutrophilic) differentiation and in the etiology of myeloid leukemia.

Since the late 1970's, progress has been made toward the development of general methods for introducing cloned gene sequences into eukaryotic cells (e.g., mammalian cells). As a result, genetic therapies whereby heterologous genes are introduced into, and expressed by host cells, are now possible. However, to date, little is known about the factors governing cell commitment in hematopoiesis because hematopoietic stem cells have proven difficult to genetically engineer. For example, most promoters, particularly retroviral promoters, become repressed after being introduced into hematopoietic stem cells. Therefore, heterologous genes which are under the control of heterologous promoters are not expressed.

SUMMARY OF THE INVENTION

The present invention relates to hematopoietic stem cell specific gene expression. The invention includes hematopoietic stem cell specific gene expression under the control of either a hematopoietic stem cell specific promoter or a hematopoietic stem cell specific enhancer or both.

The present invention includes a hematopoietic stem cell specific promoter which comprises a DNA sequence that directs the expression of a gene which is preferentially expressed in hematopoietic stem cells. A preferred promoter is the 4.5 kb sequence which is upstream of (5' of) the human CD34 gene. In particular, the present invention relates to portions of the 4.5 kb sequence which are sufficient to direct hematopoietic stem cell specific expression of a heterologous gene. Additionally, the invention includes constructs which contain DNA sequences sufficient to direct hematopoietic stem cell specific expression of a gene.

The present invention also includes a hematopoietic stem cell specific enhancer which comprises a DNA sequence that directs the expression of a gene which is preferentially expressed in hematopoietic stem cells. A preferred enhancer is present in a sequence which comprises an approximately 3.3 kb HindIII-HindIII fragment at the 3' end of the human gene encoding CD34. This fragment includes 802 bp of the 3' CD34 cDNA untranslated region and approximately 2.5 kb of 3' CD34 flanking sequences. In particular, the present invention relates to portions of the approximately 3.3 kb HindIII-HindIII CD34 fragment sufficient to direct hematopoietic stem cell specific expression of a heterologous gene.

The present invention further relates to a hematopoietic stem cell specific promoter-heterologous gene construct, and to a hematopoietic stem cell specific enhancer-heterologous gene construct whereby the expression of the heterologous gene is under the control of either the hematopoietic stem cell specific promoter or the hematopoietic stem cell specific enhancer, or both. In addition, the present invention relates to methods of producing a selected product in a hematopoietic stem cell. These methods include introducing into the hematopoietic stem cell a heterologous gene under the control of a hematopoietic stem cell specific promoter, or a hematopoietic stem cell specific enhancer, or both. The invention also includes cells produced by the methods described herein. Further, the invention relates to a method of expressing a selected heterologous gene product in hematopoietic stem cells of an individual, i.e., gene therapy, whereby stem cells produced by the methods described herein are introduced into an individual, wherein they express the heterologous gene under transcriptional control of a hematopoietic stem cell specific promoter or hematopoietic stem cell specific enhancer, or both.

Further, the invention includes a transgenic nonhuman mammal in which hematopoietic stem cells express a protein encoded by a heterologous gene. Under transcriptional control of a hematopoietic stem cell specific promoter or hematopoietic stem cell specific enhancer, or both.

The invention further includes a method for identifying factors which can regulate hematopoietic stem cell specific transcription.

BRIEF DESCRIPTION OF THE DRAWINGS

FIG. 4 depicts the assessment of CD34 intragenic and 3' flanking sequences for enhancer activity: a partial restriction map of the CD34 gene is depicted at the top, with the relevant restriction sites indicated (B, BamHI; E, EcoRI; H, HindIII; K, KpnI; S, SstI; X, XbaI); exons are indicated with open boxes; solid black boxes in exons 1 and 8 designate the 5' and 3' untranslated regions, respectively; three potential DNAseI hypersensitive sites are indicated by arrows; the heavy black horizontal lines below the map represent fragments inserted 5' to the CD34 promoter in the 2 kb/CD34-Luc construct; the numbers at right show the fold enhancement produced by each construct when compared to the parental 2 kb/CD34-Luc construct; the data are presented as the mean and standard error of the mean for three independent transfection experiments in RPMI-8402 cells.

DETAILED DESCRIPTION OF THE INVENTION

The present invention relates to a hematopoietic stem cell specific promoter which comprises a promoter that controls the expression of a gene which is preferentially expressed in hematopoietic stem cells. In one embodiment of the invention, the hematopoietic stem cell specific promoter is the CD34 promoter. In a preferred embodiment of the invention, the hematopoietic stem cell specific promoter has the sequence (SEQ. I.D. NO: 1):

The invention also includes a hematopoietic stem cell specific promoter whose sequence is substantially similar to, or substantially similar to a functional portion of the sequence listed above. Additionally the invention includes constructs which contain these promoters.

Further, the invention includes an isolated nucleic acid strand which hybridizes under standard conditions to all or a portion of a nucleic acid strand having the sequence listed above (SEQ. I.D. NO: 1) or its complement, and constructs containing such an isolated nucleic acid strand.

Additionally, the application is drawn to a method of producing a selected product in a hematopoietic stem cell. This is accomplished by introducing a heterologous gene encoding a selected product under the control of a hematopoietic stem cell specific promoter into a hematopoietic stem cell. The preferred hematopoietic stem cell specific promoter is the CD34 promoter.

The invention further includes a hematopoietic stem cell specific promoter-heterologous gene construct wherein expression of the heterologous gene is under the control of the hematopoietic stem cell specific promoter. In a preferred embodiment the hematopoietic stem cell specific promoter is the CD34 promoter.

The invention also includes a transgenic non-human mammal in which a hematopoietic stem cell expresses a protein encoded by a heterologous gene introduced, as a component of a hematopoietic stem cell promoter-heterologous gene construct, into the pronucleus of an embryo from which the transgenic mammal, or an ancestor of the transgenic mammal, developed.

Finally the invention includes a method for identifying factors which can regulate hematopoietic stem cell specific transcription. This is practiced by: 1) obtaining a hematopoietic stem cell which contains (e.g., has been transfected with, or is derived from a cell transfected with) a heterologous gene under the transcriptional control of a hematopoietic stem cell specific promoter (i.e., a hematopoietic stem cell promoter-heterologous gene construct); 2) contacting the cell containing the hematopoietic stem cell promoter-heterologous gene construct with a selected factor; 3) assaying for expression of the heterologous gene and comparing its expression in cells contacted with the factor with expression of the gene in cells not contacted with the factor, and thereby determining whether the expression pattern of the heterologous gene is altered in cells contacted with the factor as compared to that of cells which have not been contacted with the factor.

The present invention is based on the discovery that the human genomic region 5' of the gene encoding CD34 comprises a 4.5 kb sequence which contains a control element(s) which is capable of directing hematopoietic stem cell specific transcription of a heterologous gene in transfected hematopoietic stem cells, but not capable of directing expression in more differentiated cells of the hematopoietic cell lineage.

As further described in the Examples, it is now possible to specifically express a heterologous gene in a hematopoi-

```
TAGGATGATGGTGATGGGGAACTAAATGGGGAAATATGGAAGGTCACAGGAAAAGTTA
ACACAAGTTAGCAAAAAGTTAACATAACACAAAAAGGTCTTGCAGGAAAAAAAAAAGA
AAAGAAAAGAAAGAAAAAGTCTCCAAGAATGGTTTGGACAGCCAAAATGAATACTTAT
AGTCACGTATACCTGCTCACTCCTGACGCTTCACTCACACAGCACAGGATCTGGTG
AGGCTATCACTAAATGTGCCACATTGTGGTTAAGTTTTACCTGATTAACGAAATGCTC
ACACTTCTAAACTGAGGTCCTTACAGTAGATTCCTTTTGCAAGATTGTTACTGGCTTA
CAACTTAAAAATAAAGGAAAATCACAAGGAAAGAAAAGTGGGGAAAAAATCGGAGGAA
ACTTGCCCCTGCCCTGGCCACCGGCAAGGCTGCCACAAAGGGGTTAAAAGTTAAGTGG
AAGTGGAGCTTGAAGAAGTGGGATGGGGCCTCTCCAGAAAGCTGAACGAGGCATCTGG
AGCCCGAACAAACCTCCA
``` etic stem cell by introducing into a hematopoietic stem cell a heterologous gene which is under the control of a hematopoietic stem cell specific promoter.

For the purposes of the subject invention, the phrase "hematopoietic stem cell specific promoter" refers to a DNA sequence which functions as a transcriptional control element or elements and which directs the expression of a gene which is expressed in hematopoietic stem cells and which is not expressed in other cell types. The term "hematopoietic stem cell specific promoter" can include all or a portion of a DNA sequence which functions as a transcriptional control element. The term "hematopoietic stem cell specific promoter" is used interchangably herein with the term "stem cell promoter.

The term "hematopoietic stem cell specific enhancer" refers to a DNA sequence which functions as a transcriptional control element and which directs expression of a gene which is expressed in hematopoietic stem cells and which is not expressed in other cell types. The term can include all or a portion of a DNA sequence which functions as a hematopoietic stem cell specific enhancer. In other words, the term refers to a DNA sequence which: 1) activates, in hematopoietic stem cells, transcription from a promoter functionally linked to it; 2) operates in either orientation with respect to the promoter it activates; and 3) functions, in hematopoietic stem cells, to enhance transcription from a promoter even when located up to several thousand base pairs from that promoter. The term "enhancer" is used herein interchangeably with the term "element".

The term "functional portion" refers to DNA sequences which are of sufficient size and sequence to have the desired function (i.e. the ability to cause tissue specific expression of a heterologous gene).

A sequence which is "substantially similar" to another sequence is one which has a substantial degree of DNA or RNA sequence homology to the other sequence. A sequence which "hybridizes" with another is one which has sufficient nucleic acid sequence complementarity to allow the formation of base pairing and hydrogen bonding under standard DNA hybridization conditions.

The term "construct" includes linear or circular recombinant DNA sequences which include at least a functional portion of the stem cell promoter and DNA encoding a heterologous gene. The stem cell promoter is functionally linked to the heterologous gene in the constructs described herein.

"Heterologous DNA" or "heterologous gene" refer to DNA sequences, or a gene, which are not normally present in the cell as obtained, or which are not ordinarily functionally associated with a hematopoietic stem cell specific promoter region in the cell as obtained, or which are not ordinarily functionally associated with a hematopoietic stem cell specific enhancer in the cell as obtained.

A hematopoietic stem cell promoter or enhancer of the present invention can be obtained (isolated) from a naturally-occurring source, or it can be produced using any of a variety of techniques, such as genetic engineering or cloning methods, PCR amplification or synthetic techniques. Although the promoter and enhancer described herein are of human origin, stem cell promoters and enhancers can be derived from another source (or have the sequence of a hematopoietic cell type specific promoter or enhancer of other than human origin), such as from murine origin.

The CD34 promoter is a strong promoter of expression in hematopoietic stem cells. Therefore, in addition to specific expression, the CD34 promoter offers the advantage of high level of expression of a desired product in hematopoietic stem cell.

The 4.5 kb 5' upstream region of the CD34 gene contains information necessary for tissue specific expression of a heterologous gene. However, the 5' upstream region can be further characterized and divided into regulatory domains. For example, regulatory domains of a hematopoietic stem cell specific promoter, which modify transcriptional activity of neighboring regions, have been identified by transfecting the hematopoietic stem cell with DNA constructs containing varying lengths of the 5' upstream region and a heterologous gene and detecting alterations in expression of the heterologous gene. These identified regulatory domains of the 5' upstream region can be used to identify other hematopoietic stem cell specific promoters. Similarly, the approximately 3.3 kb CD34 HindIII-HindIII fragment spanning 802 bp of the 3' untranslated region and approximately 2.5 kb of 3' CD34 flanking DNA contains information necessary for tissue specific expression of a heterologous gene. The hematopoietic stem cell specific enhancer located within this region can be used to identify other hematopoietic stem cell specific enhancers or promoters.

Stem cell specific promoter or enhancer-heterologous gene constructs can be used to screen for and identify regulators of cell specific transcription. For example, hematopoietic stem cells may be transfected with DNA constructs containing functional portions of a hematopoietic stem cell specific promoter or enhancer and a heterologous gene in the presence of a variety of potential transcription factors; the ability of the transcription factors to alter the function of the promoter or the enhancer may then be tested by assaying for alterations in expression of the heterologous gene.

Figure 1A:
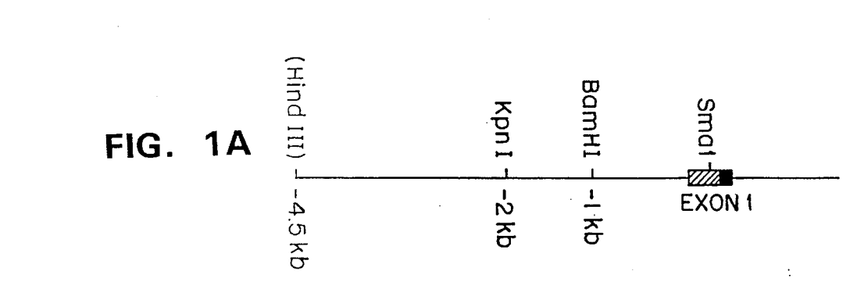
FIG. 1A shows a partial restriction map and the structure of the 5' flanking region of the CD34 gene: the coding region is designated by solid bars and the 5' untranslated region is designated by the stippled box; the HindIII restriction site at −4.5 kb is derived from the pWE15 cosmid.
Figure 1B:
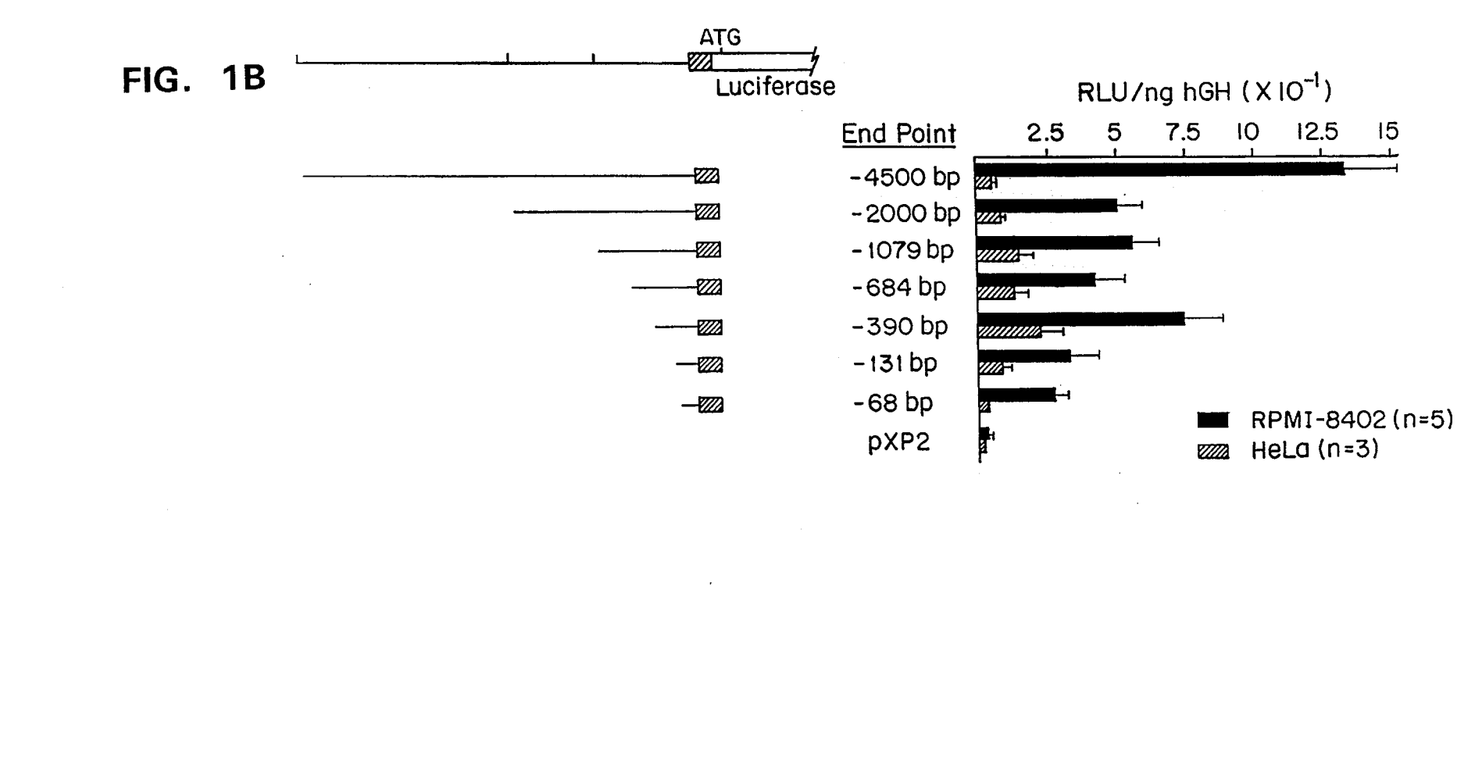
FIG. 1B is a graphic representation of luciferase activities of seven different CD34-luciferase constructs (representing 4.5 kb of 5' CD34 flanking DNA, and six shorter portions of this region, operatively linked to a gene encoding luciferase) transiently expressed in either RPMI-8402 cells (dark stipples) or HeLa cells (light stipples).

The following Examples demonstrate that the CD34 gene, encoding a hematopoietic stem cell specific marker, is transcriptionally active in CD34$^+$ KMT-2 and RPMI-8402 cells, and inactive in CD34$^-$ U937, HL-60 and HeLa cells. The CD34 promoter region was isolated and shown to be 30-fold more active in RPMI-8402 cells when compared to nonhematopoietic HeLa cells. Deletion analysis of the CD34 promoter region showed at least two regions of 5' CD34 flanking DNA which potentially contain positive regulatory element(s). The largest reduction in promoter activity was produced by deleting sequences between −4.5 kb and −2 kb (FIG. 1B). This deletion is of particular interest because the observed decrease in promoter strength occurred only in CD34$^+$ RPMI-8402 cells and not in HeLa cells. This observation is in sharp contrast to results observed with the deletion of sequences between −390 and −131 bp, which reduced the promoter activity in both RPMI-8402 and CD34$^-$ HeLa cells.

Also described are hematopoietic stem cell specific promoter-heterologous gene constructs comprising portions of the CD34 promoter region and the gene encoding luciferase. Further described are hematopoietic stem cell specific enhancer-heterologous gene constructs which comprise the CD34 enhancer and, in order to direct expression of heterologous luciferase gene, either the CD34 promoter region or the TK promoter.

MATERIALS AND METHODS

Cell Culture

T-lymphoblastic RMPI-8402 (C. C. Huang et al., *J. Natl. Cancer Inst.* 53:655 (1974)) (provided by Dr. J. L. Pauly, Roswell Park Cancer Institute, Buffalo, N.Y.), monocytic U937 (ATCC No. CRL 1593), and promyelocytic HL-60 cells (ATCC No. CCL 240) were maintained in RPMI-1640 medium (GIBCO, Grand Island, N.Y.) supplemented with 10% fetal calf serum (Hyclone, Logan, Utah) and 2 mmol/L L-glutamine (GIBCO). Myelomonocytic KMT-2 cells (S. Tamura et al., *Blood* 76:501 (1990)) (provided by Dr. T. Suda, Jichi Medical School, Tochigi-Ken, Japan) were grown in RPMI-1640 (GIBCO) supplemented with 10% fetal calf serum (Hyclone), 2 mmol/L L-glutamine (GIBCO) and 5 ng/ml rhIL-3 and 5 ng/ml rhGM-CSF (Gift of Dr. J. Williams, Genzyme, Cambridge, Mass.). HeLa cells (ATCC No. CCL 2), a cervical carcinoma line, were grown in Dulbecco's Modified Eagle Media (DMEM; GIBCO) supplemented with 10% newborn calf serum (GIBCO) and 2 mmol/L L-glutamine (Gibco).

Nuclear Run-on Transcription Assays

Nuclear run-on assays were performed as previously described. (A. B. Satterthwaite et al., *Blood* 75:2299 (1990)). Slot blots were performed using the following DNAs: the plasmid CDM8 (B. Seed, *Nature* 329:840 (1987)); a 1.5 kb XbaI fragment of the human CD34 cDNA containing the complete coding region in the plasmid CDM7 (D. L. Simmons et al., *J. Immunol.* 148:267 (1992)); a 1.6 kb EcoRI-ClaI fragment of the human c-myc exon 3 in the plasmid pSP65 (R. Dalla Favera et al., *Proc. Natl. Acad. Sci. USA* 79:6497 (1982)). Autoradiograms were exposed at −80° C. using a Dupont Lightning Plus intensifying screen and quantitated with an LKB scanning densitometer.

Plasmids for Transient Transfection Experiments

The promoterless luciferase plasmid pXP2 (S. K. Nordeen, *BioTechniques* 6:454 (1988)) was used for all promoter studies. A thymidine kinase (TK) construct, pT81-Luc ((S. K. Nordeen, *BioTechniques* 6:454 (1988)), containing base pairs −81 to +52 of the TK promoter was used in enhancer studies. A cytomegalovirus-human growth hormone (CMV-hGH) plasmid, used as an internal standard in transfections, was provided by Dr. Leonard Zon (Children's Hospital Medical Center, Boston, Mass.).

Figure 5:
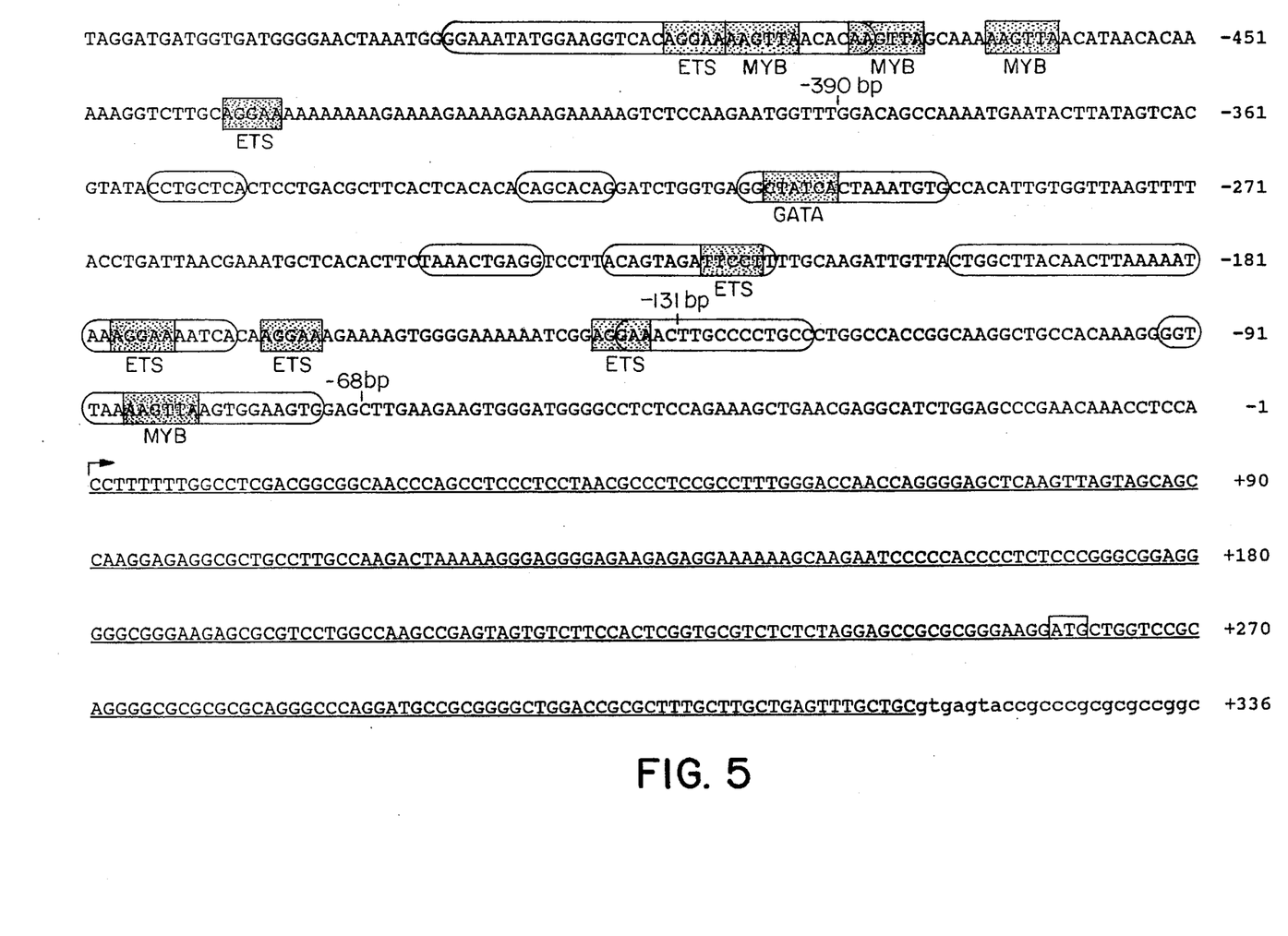
FIG. 5 is the DNA sequence (SEQ. I.D. NO: 4) of the human CD34 promoter and 5' flanking DNA: the 5' flanking DNA of the human CD34 promoter was compared to the published murine CD34 sequence, and regions of the human promoter with greater than 80% similarity to the murine promoter are circled; potential binding sites are indicated by shaded boxes; the transcriptional start site is indicated by an arrow at +1 and sequences from exon 1 are underlined; the open box at +259 is used to designate the translation start site; intronic sequences are shown in lowercase characters; the end points of the deletions are indicated by number and vertical lines.

A 2.4 kb KpnI-ApaI CD34 genomic fragment was obtained from the cosmid CD34-2A (A. B. Satterthwaite et al., *Genomics* 12:788, (1992)) and cloned into KpnI-ApaI digested pSL1180 in order to add convenient restriction sites to the ends of the fragment (Pharmacia, Uppsala, Sweden). A CD34-luciferase construct was prepared by subcloning the HindIII-SmaI fragment from the pSL1180 subclone into the pXP2 luciferase plasmid containing a HindIII end and a Klenow filled in BglII site. The resulting construct contained approximately 2 kb of 5' CD34 flanking DNA and extended to +175 bp, where +1 denotes the transcriptional start site of CD34 (FIG. 5). In addition, a 4.7 kb HindIII-SmaI genomic fragment, obtained from cosmid CD34-2A, was subcloned into pXP2 containing a HindIII end and a blunt ended SstI site. The 5 HindIII-SmaI/CD34-Luc construct contains 4.5 kb of 5' flanking DNA and 175 bp of the 5' untranslated region (FIG. 5). The HindIII site used in this subcloning is derived from the pWE15 cosmid (Stratagene). A construct containing 1089 bp of 5' CD34 flanking DNA was produced by digesting the 4.5 kb/CD34-luc plasmid with BamHI and then religating the remaining plasmid.

Unidirectional deletions of the 2 kb/CD34-luciferase construct were prepared using Exonuclease III using standard techniques (see, e.g., S. Henikoff, *Gene* 28:351 (1984)). PCR was used to produce a deletion mutant containing 68 bp of 5' flanking DNA. A 5' primer, which hybridized starting at basepair −68 (5' GGGGATCCTTGAAG AAGTGG-GATGGGGCCTCT) (SEQ ID NO: 2), and a 3' primer, which hybridized at +87 (5' GCTACTAACTTGAGCTC) (SEQ ID NO: 3), were incubated with a CD34 genomic subclone under standard PCR conditions (F. M. Ausubel et al., *Current Protocols in Molecular Biology*, Green Publishing Associates and Wiley Interscience, New York, pp. 15.03–15.17, (1989)). The PCR product was digested with BamHI and SstI and subcloned into BamHI-SstI digested 1089 bp/CD34-Luc. Dideoxy DNA sequence analysis (F. Sanger et al., *Proc. Natl. Acad, Sci. USA* 74:5463 (1977)) was performed to identify the positions of the ExoIII end points and to confirm the sequence of the −68 bp PCR deletion.

A series of Rous sarcoma virus (RSV) enhancer containing constructs was also prepared. A 500 bp EcoRI fragment containing the RSV enhancer obtained from the pRSVneo plasmid (provided by Dr. Tim Ley, Washington University Medical Center, St. Louis, Mo.), was digested with the klenow fragment of DNA polymerase I to create blunt ends, and subcloned into the similarly blunt ended ApaI site of pXP2. The resulting construct contained the RSV enhancer situated 3' to the luciferase gene. In a similar manner, the RSV enhancer was also added to the pT81-Luc and the 2 kb/CD34-Luc plasmids.

Transient Transfections

DNA was prepared and transfected as previously described using $2 \times 10^7$ cells per transfection (H. L. Pahl et al., *Exp. Heme.* 19:1038 (1991)). RPMI-8402 cells were electroporated at 270 volts and 960 μF, while HeLa cells were electroporated at 150 volts and 960 μF. Luciferase activity was measured in relative light units (RLU) 6 hours post-transfection using an Analytical Luminescence Laboratory luminometer (San Diego, Calif.) as described (H. L. Pahl et al., *Exp. Heme.* 19:1038 (1991)). All transfection experiments contained sample DNAs equimolar to 20 μg of pXP2 and 2 μg of the CMV-hGH internal standard. Growth hormone production was measured by assaying the media of transfected cells with a commercially available RIA kit (Nicol's Institute, San Juan Capistrano, Calif.). The RLU from individual transfections were normalized for transfection efficiency based on the amount, in nanograms, of growth hormone produced by 2 μg of the CMV-hGH internal standard. Individual transfections were repeated at least three times and the results are reported as RLU per ng of hGH ±the standard error of the mean.

DNA Methylation Analysis

Genomic DNA was isolated from KMT-2, RPMI-8402, U937 and HL-60 cells by standard techniques (F. M. Ausubel et al., *Current Protocols in Molecular Biology*, Green Publishing Associates and Wiley Interscience, New York, pp. 2.2.1–2.2.3, (1989)). Ten micrograms of each DNA was digested overnight with a 10-fold excess of EcoRI (BRL, Bethesda, Md.), then phenol/chloroform/isoamyl alcohol (24:24:1, v:v:v) extracted and ethanol precipitated. The EcoRI digested DNAs were subsequently digested overnight with an excess of either HpaII, MspI, or HhaI (New England Biolabs, Beverly, Mass.) following the manufacturers' recommendations. Digested DNAs were ethanol precipitated and resuspended in TE buffer at a concentration of 1 mg/ml. The DNAs were electrophoresed on Tris-acetate gels and transferred to Zetaprobe membrane (Bio-Rad, Richmond, Calif.) in 10X SSC (1X is 0.15 mol/L NaCl, 0.015 mol/L sodium citrate). The membrane was probed with a $^{32}$P-random prime labeled 750 bp SstI-EcoRI genomic CD34 fragment, encompassing the exon 1 and intron 1 junction (A. B. Satterthwaite et al., *Genomics* 12:788 (1992)). Hybridization was performed at 65° C. in 7% SDS, 40 mmol/L NaPO$_4$ (pH 7.2), 1 mmol/L EDTA for 24 hours, after which the membrane was washed in 2X SSC, 0.1% SDS for 10 minutes at room temperature followed by 0.1X SSC, 0.1% SDS for one hour at 65° C. As a control for complete digestion, the blot was stripped and reprobed with a 414 bp genomic PstI-PstI c-myc probe from exon 2 (J. Battey et al., *Cell* 34:779 (1983)), which has been shown to have an invariant pattern of methylation in a variety of cells (M. Lubbert et al., *Leukemia* 5:533 (1991)).

EXAMPLES

Example 1

The CD34 Gene is Transcriptionally Regulated in Tissue Culture Cells

To determine if the cell type specificity of the CD34 gene is regulated at the level of transcription, we performed nuclear run-on assays with CD34$^+$ KMT-2 and RPMI-8402 cells and CD34$^-$ HL-60, U937 and HeLa cells. In nuclear run-ons using KMT-2 and RPMI-8402 cells, the amount of hybridization to the CD34 cDNA was 17-fold greater than the amount seen with empty CDM8 plasmid control. In U937, HL-60, and HeLa cells, no significant hybridization was seen to the CD34 cDNA when compared to the empty CDM8 plasmid control. Hybridization to the myc exon 3 positive control was significantly above background levels in all experiments. These data indicate that the CD34 gene is transcriptionally active in CD34$^+$ cells and inactive in CD34$^-$ cells.

Example 2

Deletion Analysis of the CD34 Promoter Demonstrates the Presence of a Number of Positive Regulatory Elements We had previously identified the CD34 transcriptional start site using RNase protection (A. B. Satterthwaite et al., *Genomics* 12:788 (1992)) and 5' RACE (rapid amplification of cDNA ends) (D. L. Simmons et al., *J. Immunol*, 148:267 (1992)). This information was used to subclone a CD34 genomic fragment containing 4.5 kb of 5' flanking DNA and 175 bp of the 5' untranslated region (FIG. 1A) into the pXP2 promoterless luciferase vector (FIG. 1B). When this construct was used to transiently transfect RPMI-8402 cells, luciferase was expressed at levels greater than 30-fold above pXP2 control levels (134±22 RLU/ng hGH [n=5] versus 4±2 RLU/ng hGH [n=5], respectively) (FIG. 1B).

In order to localize the cis-elements required for CD34 promoter activity, we produced a series of six deletion mutants in the 4.5 kb/CD34-Luc construct using convenient restriction sites, exonuclease III and PCR (FIG. 1B). Deletion of sequences between −4.5 kb and −2 kb decreased the promoter activity by nearly 3-fold to 50±11 RLU/ng hGH (n=5). This drop in activity was observed in five independent experiments using multiple preparations of DNA. No significant alteration in promoter activity was observed when sequences between −2 kb and −390 bp were deleted (FIG. 1B). Further deletion to −131 bp produced a greater than two-fold drop in luciferase activity when compared to the −390 bp construct (76±16 [n=5] versus 34±10 [n=5]). This drop in activity was observed in five independent transfections. A final deletion mutant was produced by PCR in order to remove a potential myb binding-site at −87 bp. Despite having only 68 bp of 5' flanking DNA, the amount of luciferase activity was not significantly different from the amount of activity obtained with the 131 bp/CD34-Luc construct (FIG. 1B). These data demonstrate the presence of a number of positive transcriptional regulatory elements within the 4500 bp of flanking DNA 5' of the gene encoding CD34.

Example 3

The CD34 Promoter is Expressed at Significantly Higher Levels in CD34$^+$ RPMI-8402 Cells than in CD34$^-$ HeLa Cells To analyze the specificity of the CD34 promoter, we transfected the seven CD34-Luc constructs depicted in FIG. 1B into the cervical carcinoma cell line, HeLa. The CD34-Luc constructs were significantly less active in HeLa cells when compared to RPMI-8402 cells (FIG. 1B), suggesting that the elements required for hematopoietic-specific expression were present in these constructs. The promoter activity of the 4.5 kb/CD34-Luc construct was approximately 30-fold greater in RPMI-8302 cells when compared to the activity in HeLa cells (FIG. 1B). Levels of promoter activity similar to that of RPMI-8402 cells were observed when the CD34-Luc constructs were transfected into U937 cells, which are CD34$^-$ by Northern blot analysis but CD34$^+$ by reverse transcriptase-PCR (data not shown).

To verify that cotransfection with the CMV-hGH construct was a useful control which accurately corrected for differences in transfection efficiency between RPMI-8402 and HeLa cells, we directly measured the relative amount of transfected DNA present each cell line. RPMI-8402 and HeLa cells were cotransfected with the 4.5 kb/CD34-Luc and CMV-hGH constructs as described in the Materials and Methods. Luciferase assays were performed on 30% of the transfected cells (Table 1). Comparison of the uncorrected RLU indicated that the 4.5 kb/CD34-Luc construct produced 38-times more luciferase activity in the transfected RPMI-8402 cells (Table 1). Since the two cell lines were equally transfectable, as judged by growth hormone production (Table 1), normalization with growth hormone did not significantly alter the relative luciferase activities (Table 1). Based on the growth hormone corrected RLU, the 4.5 kb/CD34-Luc construct was 32-fold more active in RPMI-8402 cells (Table 1). Transfected DNA was isolated from the remaining cells using Hirt extracts, digested with EcoRI and Southern blotted. The relative amount of transfected DNA was determined by hybridization with a random primed luciferase probe, which detected a 2.7 kb EcoRI band from the 4.5 kb/CD34-Luc construct. After correcting for recovery using the control oligonucleotide probe, it was determined that the HeLa cells contained 65 percent as much transfected DNA when compared to the RPMI-8402 cells (e.g., Table 1). Normalization of the uncorrected luciferase activities with the Hirt extract data indicated that the 4.5 kb/CD34-Luc construct was 25-times more active in RPMI-8402 cells than in HeLa cells, essentially the same result as that obtained using growth hormone (Table 1).

TABLE 1

COMPARISON OF CORRECTION METHODS.

| | Uncorrected Relative Light Units (RLU) | Growth Hormone Produced (ng) | Growth Hormone Corrected RLU | Relative Amount of Hirt DNA Recovered | Hirt Extract Corrected RLU |
|---|---|---|---|---|---|
| HeLa | 440 | 92(0.84X) | 524 | 0.65X | 677 |
| RPMI-8402 | 16979 | 110(1X) | 16979 | 1X | 16979 |

RPMI-8402 and HeLa cells were cotransfected with the 4.5 kb/CD34-Luc construct and CMV-hGh as described in the Materials and Methods.
Luciferase assays were performed on 30% of the cells,m while the transfected DNA was isolated from the remaining cells by Hirt extraction.
Luciferase activities (in RLU) were corrected using both growth hormone produciton and the Hirt extract data from FIG. 3.
These data are from a parallel experiment using an equal number of RPMI-8402 and HeLa cells.

To summarize, these data show that the CD34-Luc constructs were significantly more active in CD34$^+$ RPMI-8402 cells when compared to nonhematopoietic HeLa cells (FIG. 1B). However, when the constructs were compared in CD34$^-$ U937 cells and CD34$^+$ RPMI-8402 cells, no significant difference in activities was observed (data not shown). A low level of CD34-Luc expression in U937 cells would not be unexpected, because we are able to detect low levels of CD34 mRNA in these cells using RT-PCR (data not shown). Based on our run-on data, however,one would expect the constructs to be significantly less active in U937 cells when compared to RPMI-8402 cells. The methylation of the CD34 CpG island in HL-60 and U937 cells (discussed below) provides a possible explanation for our transient expression results. Work by Thompson and coworkers (J. P. Thompson et al., *J. Biol. Chem.* 266:2549 (1991)) has shown that unmethylated copies of the Proel(I) collagen gene are transcriptionally active when transfected into cells containing a methylated and inactive endogenous gene. Therefore, it would not be unreasonable to observe expression of the CD34-Luc constructs in U937 cells, provided U937 cells are capable of expressing the CD34 gene and are CD34$^-$ due to the methylation of the endogenous CD34 gene. Alternatively, it is possible that our CD34-Luc constructs lack an additional enhancer or silencer element which is responsible for providing tissue-specificity within the hematopoietic system. In either case, our data indicate that the CD34 3' enhancer element(s) may contribute to the specificity of the CD34 promoter, since we observed no enhancement with this element(s) in U937 cells.

Example 4

Figure 2:
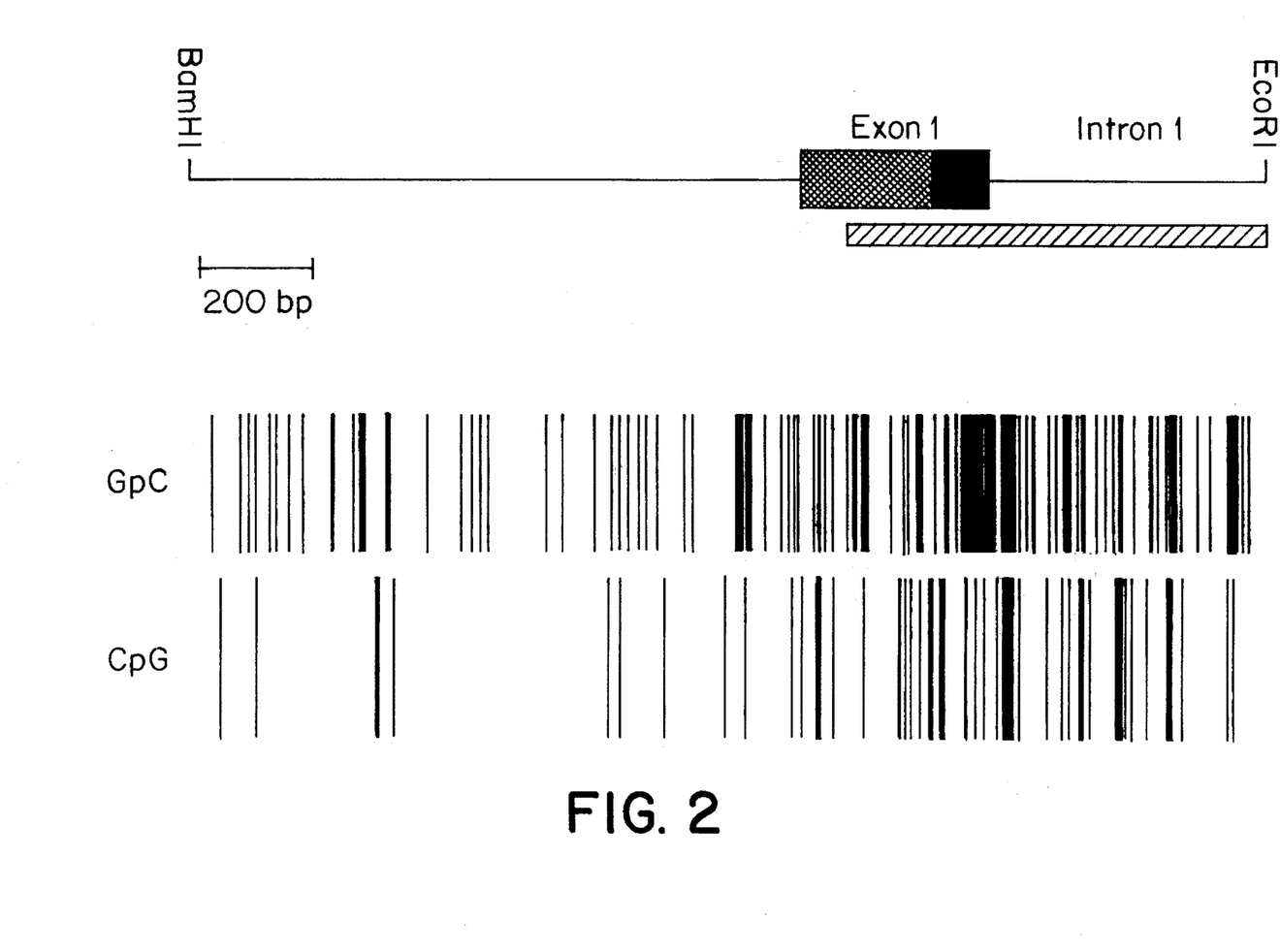
FIG. 2 is a map of the CD34 5' CpG island within the BamH1-EcoRI fragment from the CD34 gene (top row) showing the locations of GpC and CpG dinucleotides along the map: Exon 1 is designated by the box; the 5' untranslated region is indicated by the stippled box; the coding region is designated by the solid line; the 750 bp SstI-EcoRI fragment used in Southern blot analysis is designated by the stippled box immediately below the map.

Demethylation of the CD34 5' CpG Island Correlates with CD34 Expression in Hematopoietic Cell Lines Since the CD34-Luc constructs were also expressed in CD34-U937 Cells, we examined whether additional regulatory processes were responsible for CD34 regulation in these cells. In mammalian DNA, CpG dinucleotides are found one fifth as frequently as GpC pairs (Y. H. Edwards, *Phil. Trans. R Soc. Lond.* 326B:207 (1990)). We have identified a CpG island at the 5' end of the CD34 gene within the final 160 bp of exon 1 and the first 140 bp of intron 1, this region has a 72% G+C content and a CpG to GpC ratio of 0.70 (FIG. 2). A similar G+C rich region has been observed in the 5' end of the murine CD34 gene (A. B. Satterthwaite et al., *Genomics* 12:788 (1992)). Since the demethylation of CpG islands has been shown to correlate with expression of tissue-specific genes (Y. Gruenbaum et al., *FEBS Lett*, 124:67 (1981); W. Doerfler, *Ann. Rev. Biochem.* 52:93 (1983)), we examined the methylation status of the CD34 gene in CD34$^+$ and CD34$^-$ hematopoietic cell lines using two methylation sensitive restriction endonucleases (HhaI and HpaII).

Genomic DNA from the CD34$^-$ HL-60 and U937 cells was digested with EcoRI followed by either HhaI or HpaII. Hybridization of the Southern blotted DNAs with a 750 bp SstI-EcoRI genomic CD34 probe produced a 4 kb band in all samples, indicating that the CpG island is heavily methylated in HL-60 and U937 cells. The same probe detected a band of approximately 200 bp in the EcoRI-HhaI digested DNA from CD34$^+$ KMT-2 and RPMI-8402 cells, While two bands of approximately 250 bp and 350 bp were observed in KMT-2 and RPMI-8402 DNA digested with EcoRI and HpaII. These results are consistent with the complete demethylation of the CpG island in the two CD34$^+$ cell lines. To rule out the possibility that the observed differences were due to a polymorphism, the DNAs were also digested with the methylation insensitive enzyme MspI, which cleaves the same site as HpaII. Hybridization with the 750 bp SstI-EcoRI probe detected two bands at approximately 250 bp and 350 bp in all samples digested with EcoRI and MspI, indicating that a restriction length polymorphism was not responsible for the differences observed between DNAs from CD34$^+$ and CD34$^-$ cell lines when digested with the HpaII enzyme. From these data we concluded that there is a correlation between CD34 expression and demethylation of the CD34 5' CpG island in hematopoietic cell lines.

Example 5

The 3' End of the CD34 Gene has cell Type-Specific Enhancing Activity

Figure 3:
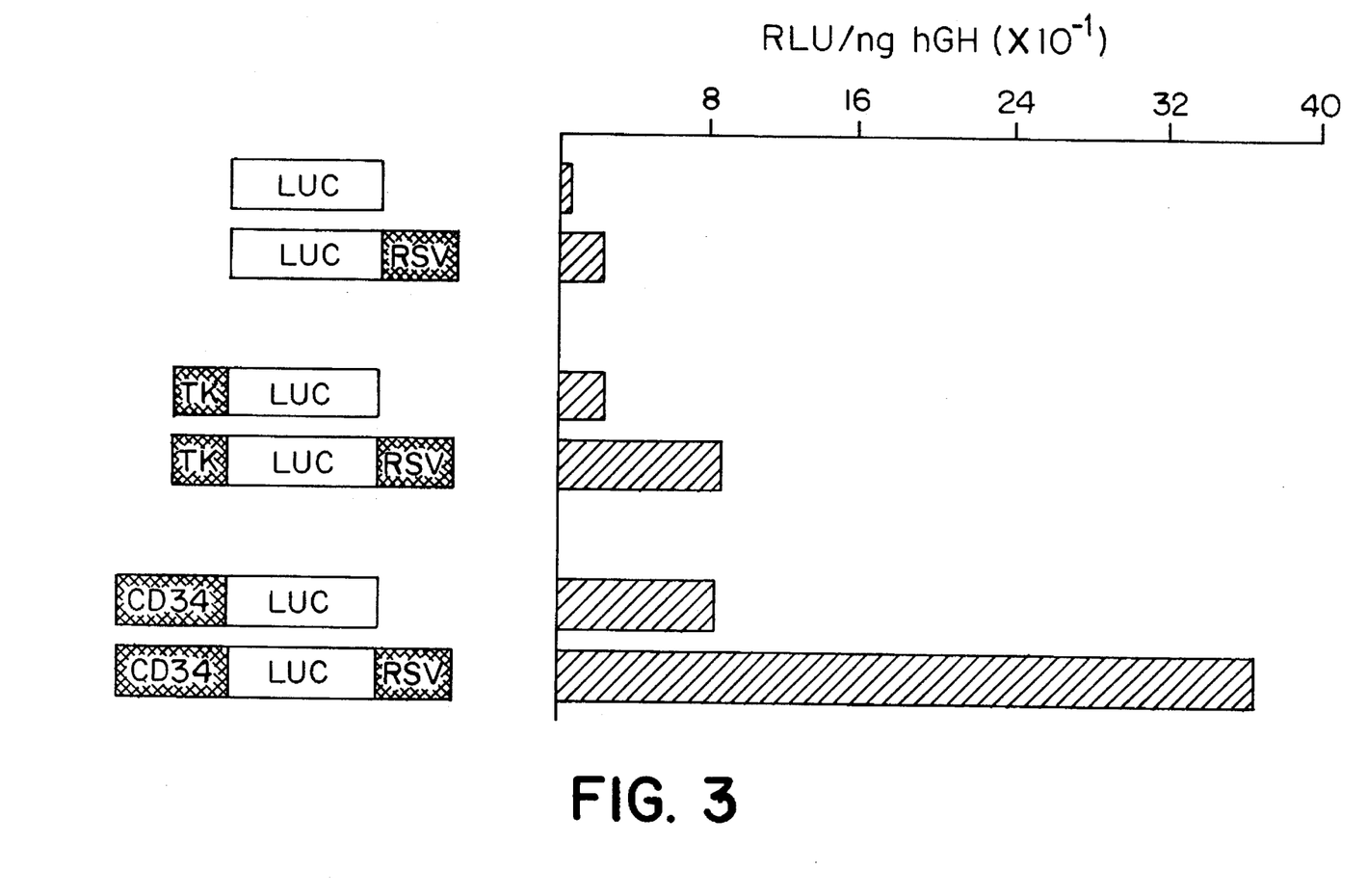
FIG. 3 is a graphic representation of enhancement of TK-luciferase and CD34-luciferase activity by the Rous sarcoma retroviral (RSV) enhancer: the RSV constructs and corresponding parental constructs are depicted on the left; the data represent hGH corrected RLU from a representative experiment.

Because the CD34-Luc constructs were active in transfection experiments in both RPMI-8402 cells (CD34$^+$) and U937 cells (CD34$^-$ by Northern blot), we looked for the presence of an additional hematopoietic cell type-specific enhancer. We first examined whether a 2 kb CD34 promoter construct was capable of responding to a viral enhancer. A series of plasmids containing the RSV enhancer inserted 3' to the luciferase gene was constructed and transfected into RPMI-8402 cells (FIG. 3). The presence of the RSV enhancer in the TK-Luc construct produced a greater than 3-fold enhancement in luciferase activity (FIG. 3). Similarly, an almost 5-fold enhancement in 2 kb/CD34-Luc activity was observed in the presence of the RSV enhancer (FIG. 3). A similar level of enhancement was observed when the RSV-containing construct was transiently transfected into HeLa cells (data not shown). These values are similar to those observed by Clevers and coworkers (H. Clevers et al., EMBO. J. 8:2527 (1989)) with a TCR-ε/CAT construct containing a 3' RSV enhancer. Based on these data, we concluded that the CD34 promoter was capable of responding to an enhancer.

Figure 4:
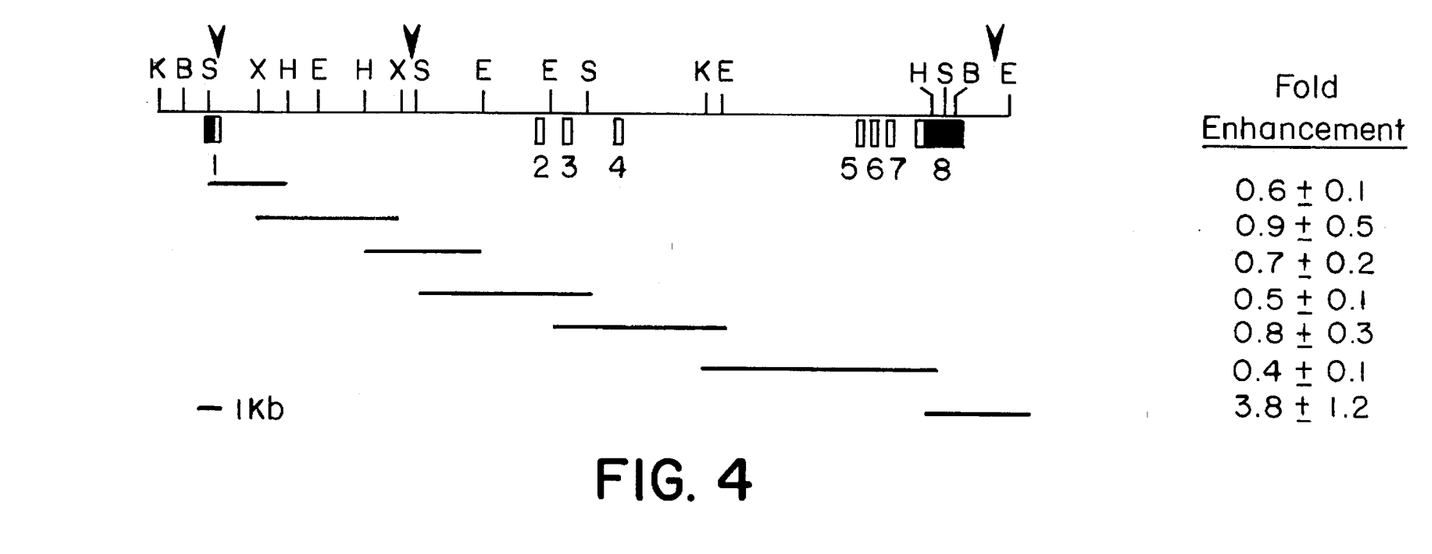

Because the presence of DNAseI hypersensitive sites is often indicative of enhancer regions (U. Pauli, et al., Proc. Natl. Acad. Sci. USA 85:16 (1988)), we performed DNAseI hypersensitivity studies with CD34$^+$ and CD34$^-$ cell lines in order to localize any potentially strong enhancers. After examining the entire CD34 gene as well as the 5' and 3' flanking sequences, we were able to identify three weak DNAseI hypersensitive sites in exon 1, intron 1 and approximately 2 kb 3' of the CD34 gene (data not shown); no hypersensitive sites were found within the first 9 kb of 5' upstream sequences. DNA fragments containing these regions were inserted 5' to the CD34 promoter of the 2 kb/CD34-Luc construct. After transient expression in RPMI-8402 cells, the luciferase activity of these constructs was compared to the parental CD34-Luc construct. We were able to demonstrate enhancing activity only in the construct containing sequences from the 3' end of the CD34 gene (FIG. 4). A construct containing 802 bp of the 3' untranslated region and 2.5 kb of 3' flanking DNA produced a 3 to 6-fold enhancement in luciferase activity when compared to the 2 kb/CD34-Luc construct (mean±SEM; 3.8±1.2 [n=3]. Similar results were obtained with CD34$^+$ KMT-2 cells. In contrast, no enhancement was observed when this construct was transiently transfected into HeLa cells (0.9±0.1 fold enhancement [n=3]). In U937 cells and in C15 eosinophilic HL-60 cells (another CD34$^-$ hematopoietic cell line), using either the CD34 or the thymidine kinase promoters, we were unable to detect any enhancing activity with the 3' CD34 element(s)in two independent experiments (data not shown). These data suggest that the 3' enhancer is cell-type specific, with the level of enhancement being similar to the levels of enhancement seen with previously characterized enhancers (H. Clevers et al., EMBO. J. 8:2527, (1989); A. R. Brooks et al., J. Biol. Chem. 266:7848 (1991); N. J. Hole et al., J. Immunol. 146:4377 (1991)).

Therefore, we have demonstrated the presence of a 3' element(s) which produced a 3–6 fold enhancement in CD34-Luc activity when transiently expressed in CD34$^+$ RPMI-8402 cells (FIG. 4) and KMT-2 cells (data not shown). The same element(s) failed to increase the activity of the CD34 promoter in CD34$^-$ HeLa, U937 and C15 HL-60 cells, suggesting that the element(s) is cell type-specific. The observed cell type specificity of this element(s) is unique to the CD34 3' element, because the RSV enhancer worked in both RPMI-8402 and Hela cells.

We also examined the remaining intragenic sequences for enhancing activity. Three to 8 kb overlapping CD34 genomic DNA fragments, encompassing all 27 kb of CD34 intragenic DNA, were subcloned into the 2 kb/CD34-Luc construct (FIG. 4). No significant enhancement in reporter gene activity was observed when these constructs were transiently transfected into RPMI-8402 cells (FIG. 4).

Equivalents

Those skilled in the art will recognize, or be able to ascertain using no more than routine experimentation, many equivalents to the specific embodiments described herein. Such equivalents are intended to be encompassed by the following claims.

We claim:

1. A promoter of the CD34 gene comprising all or a functional portion of an isolated or recombinant SEQ ID No: 1 which directs the expression of a gene in hematopoietic stem cells.

2. A hematopoietic stem cell specific promoter comprising an isolated or recombinant DNA sequence of the 4,500 base pairs of DNA flanking and 5' of the gene encoding the human hematopoietic stem cell specific gene product, CD34, wherein said sequence directs the expression of a gene in hematopoietic stem cells.

3. A promoter of the CD34 gene comprising an isolated or recombinant double stranded DNA molecule wherein one strand is all or a functional portion of the following DNA sequence (SEQ ID NO: 1)

```
TAGGATGATGGTGATGGGGAACTAAATGGGGAAATATGGAAGGTCACAGGAAA
AGTTAACACAAGTTAGCAAAAAGTTAACATAACACAAAAAGGTCTTGCAGGAA
AAAAAAAAGAAAAGAAAAGAAAGAAAAAGTCTCCAAGAATGGTTTGGACAGCC
AAAATGAATACTTATAGTCACGTATACCTGCTCACTCCTGACGCTTCACTCAC
ACACAGCACAGGATCTGGTGAGGCTATCACTAAATGTGCCACATTGTGGTTAA
GTTTTACCTGATTAACGAAATGCTCACACTTCTAAACTGAGGTCCTTACAGTA
GATTCCTTTTGCAAGATTGTTACTGGCTTACAACTTAAAAATAAAGGAAAATC
ACAAGGAAAGAAAAGTGGGGAAAAAATCGGAGGAAACTTGCCCCTGCCCTGGC
CACCGGCAAGGCTGCCACAAAGGGGTTAAAAGTTAAGTGGAAGTGGAGCTTGA
AGAAGTGGGATGGGGCCTCTCCAGAAAGCTGAACGAGGCATCTGGAGCCCGAA
CAAACCTCCA.
```

4. An enhancer of the CD34 gene comprising an isolated or recombinant DNA sequence which is all or a functional portion of the approximately 3.3 kb HindIII-HindIII digestion fragment comprising 802 bp of the 3' untranslated region of the human CD34 gene, and approximately 2.5 kb of 3' CD34 flanking DNA and directs the expression of a gene in hematopoietic stem cells.

5. An enhancer of the CD34 gene comprising an isolated or recombinant double stranded DNA molecule wherein one strand is all or a functional portion of the approximately 3.3 kb HindIII-HindIII digestion fragment comprising 802 bp of the 3' untranslated region of the human CD34 gene, and approximately 2.5 kb of 3' CD34 flanking DNA, and directs the expression of a gene in hematopoietic stem cells.

6. A promoter-heterologous gene construct, comprising a promoter of the CD34 gene and a heterologous gene, wherein the promoter of the CD34 gene comprises all or a functional portion of an isolated or recombinant SEQ ID No: 1 and expression of the heterologous gene is under transcriptional control of the promoter of the CD34 gene, wherein said promoter directs the expression of the heterologous gene in hematopoietic stem cells.

7. A hematopoietic stem cell specific promoter-heterologous gene construct comprising a promoter of the CD34 gene and a heterologous gene, wherein expression of the heterologous gene is under transcriptional control of the promoter of the CD34 gene which is an isolated or recombinant double stranded DNA molecule wherein one strand is all or a functional portion of the DNA sequence described by SEQ ID NO: 1.

8. An enhancer-heterologous gene construct, comprising an enhancer of the CD34 gene and a heterologous gene, wherein the enhancer of the CD34 gene is all or a functional portion of the approximately 3.3kb HindIII-HindIII digestion fragment comprising 802 bp of the 3' untranslated region of the human CD34 gene, and approximately 2.5 kb of 3' CD34 flanking DNA and expression of the heterologous gene is under transcriptional control of the enhancer of the CD34 gene, which directs the expression of the heterologous gene in hematopoietic stem cells.

9. The hematopoietic stem cell specific enhancer-heterologous gene construct—comprising an enhancer of the CD34 gene and a heterologous gene, wherein expression of the heterologous gene is under transcriptional control of the enhancer of the CD34 gene which is an isolated or recombinant double stranded DNA molecule wherein one strand is all or a functional portion of an approximately 3.3 kb HindIII-HindIII digestion fragment comprising 802 bp of the 3' untranslated region of human CD34 cDNA beginning at base number 1808 of the CD34 cDNA sequence, and 2.5 kb of 3' CD34 flanking DNA.

10. A hematopoietic stem cell which expresses a heterologous gene product under transcriptional control of a promoter of the CD34 gene comprising the promoter-heterologous gene construct of claim 6 or claim 7.

11. A hematopoietic stem cell which expresses a heterologous gene product under transcriptional control of an enhancer of a CD34 gene comprising the enhancer-heterologous gene construct of claim 8 or claim 9.

12. An enhancer and promoter-heterologous gene construct which directs the expression of the heterologous gene in hematopoietic stem cells, comprising an enhancer of the CD34 gene, a promoter of the CD34 gene and a heterologous gene, wherein expression of the heterologous gene is under transcriptional control of both the enhancer of the CD34 gene and the promoter of the CD34 gene and the promoter comprises all or a functional portion of the DNA sequence described by SEQ ID NO: 1, and the enhancer comprises all or a functional portion of an approximately 3.3 kb HindIII-HindIII digestion fragment comprising 802 bp of the 3' untranslated region of the human CD34 gene, and 2.5 kb of 3' CD34 flanking DNA.

* * * * *